United States Patent [19]

Clark

[11] Patent Number: 5,521,168

[45] Date of Patent: May 28, 1996

[54] ESTROGEN METABOLITES FOR LOWERING INTRAOCULAR PRESSURE

[75] Inventor: Abbot F. Clark, Arlington, Tex.

[73] Assignee: Alcon Laboratories, Inc., Fort Worth, Tex.

[21] Appl. No.: 322,250

[22] Filed: Oct. 13, 1994

[51] Int. Cl.$^6$ .......................... A61K 31/33; A61K 31/56
[52] U.S. Cl. .......................... 514/178; 514/170; 514/913
[58] Field of Search ..................................... 514/178, 170, 514/913

[56] References Cited

U.S. PATENT DOCUMENTS 4,876,250  10/1989  Clark ........................................ 514/179
5,371,078  12/1994  Clark et al. .............................. 514/182

OTHER PUBLICATIONS

Treister, et al., *Intraocular Pressure and Outflow Facility*, Arch. Ophthal., 83, 311–318 (Mar., 1970).

Meyer, et al., *Influence of Norethynodrel With Mestranol on Intraocular Pressure in Glaucoma*, Arch. Ophthal., 75, 771–773 (Jun., 1966).

Fotsis, et al., *The Endogenous Oestrogen Metabolite 2-Methoxyestradiol Inhibits Angiogenesis and Suppresses Tumour Growth*, Letters to Nature, 368, 237–239 (Mar. 17, 1994).

*Primary Examiner*—Zohreh Fay
*Attorney, Agent, or Firm*—Sally Yeager

[57] ABSTRACT

Methods for lowering and controlling intraocular pressure using estrogen metabolites are disclosed.

11 Claims, No Drawings

ESTROGEN METABOLITES FOR LOWERING INTRAOCULAR PRESSURE

FIELD OF THE INVENTION

The present invention is directed to the use of estrogen metabolites to lower intraocular pressure (IOP).

BACKGROUND OF THE INVENTION

Treister, et al., *Intraocular Pressure and Outflow Facility*, Arch. Ophthal., Vol. 83, pp. 311–318 (March, 1970) disclose that the continuous oral treatment of normal women with mestranol (estrogen) causes a gradual decrease in IOP. Meyer, et al., *Influence of Norethynodret With Mestranol on Intraocular Pressure in Glaucoma*, Arch. Ophthal., Vol. 75, pp. 771–773 (June, 1966) disclose that oral administration of mestranol with norethynodrel to patents with primary open angle glaucoma reduces IOP. Fotsis, et al., *The Endogenous Oestrogen Metabolite 2-Methoxyoestradiol Inhibits Angiogenesis and Suppresses Tumour Growth*, Letters to Nature, Vol. 368, pp. 237–239 (Mar. 17, 1994) disclose that 2-methoxyoestradiol, an endogenous oestrogen metabolite, inhibits angiogenesis. U.S. Pat. No. 4,876,250 discloses that there may be a correlation between angiostatic activity and IOP lowering activity.

Many of the above-referenced compounds which have been found to lower IOP also have hormonal activity. It would be useful to have compounds which can be used to lower and control IOP without exhibiting any hormonal activity. The compounds of the present invention fit this criteria.

SUMMARY OF THE INVENTION

Compounds of the present invention are useful in lowering and controlling the IOP associated with glaucoma or ocular hypertension.

DETAILED DESCRIPTION OF THE PREFERRED EMBODIMENTS

The compounds of the present invention which are useful in lowering and controlling IOP are estrogen metabolites or the metabolites of estrogen analogues (hereinafter collectively "estrogen metabolites"). Without intending to be bound by any theory, the estrogen metabolites lower IOP by addressing the increased resistance to aqueous outflow at the eye's outflow facility, including the trabecular meshwork, which accompanies some forms of glaucoma and ocular hypertension. All other known methods for treating glaucoma or ocular hypertension indirectly lower IOP instead of working at the disease site. For example, beta-blockers, alpha-2 agonists, and carbonic anhydrase inhibitors lower IOP by suppressing aqueous humor formation. Muscarinic agents, such as pilocarpine and carbochol, contract the ciliary muscle causing increased aqueous outflow through the trabecular meshwork. Pilocarpine and carbochol also produce unwanted side effects, such as miosis and loss of accommodation. Prostaglandins lower IOP by increasing uveoscleral outflow. Topical ocular administration of estrogen metabolites increases aqueous humor outflow at the trabecular meshwork thus "normalizing" the outflow facility.

Preferred estrogen metabolites useful for lowering and controlling IOP have the following structure:

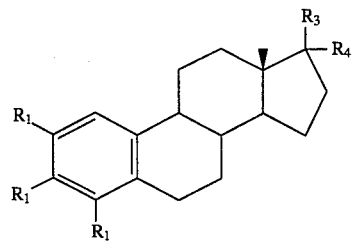

wherein:

$R_1$ is H, OH, $OR_2$, $R_2$;

$R_2$ is $C_1$–$C_6$ alkyl;

$R_3$ is OH, =O, $R_1$;

$R_4$ is $R_1$, C≡CH, C=$CH_2$; and pharmaceutically acceptable esters.

Most preferred compounds include:

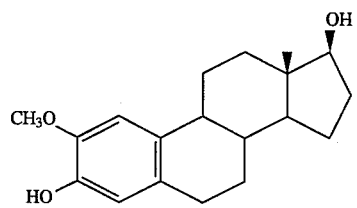

2-Methoxyestradiol

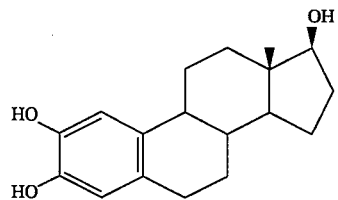

2-Hydroxyestradiol

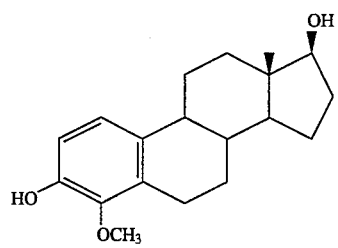

4-Methoxyestradiol

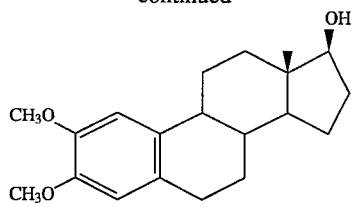

2-Methoxyestradiol 3-methyl ether

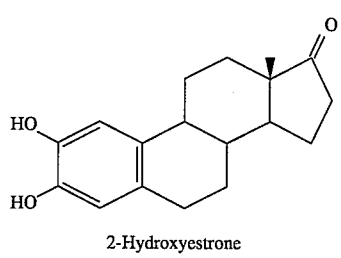

2-Hydroxyestrone

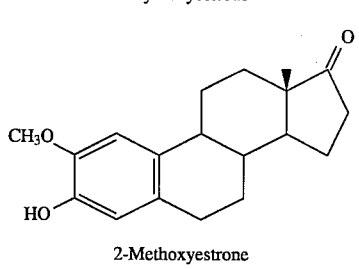

2-Methoxyestrone

The estrogen metabolites can be formulated in any suitable ophthalmic formulation such as solutions, suspensions, ointments, etc. from 0.05–5 weight volume percent (wt/vol %). The formulations can include other components known to those skilled in the art of formulating ophthalmic products. For example, the formulations can include ophthalmically acceptable preservatives, surfactants, viscosity enhancers, penetration enhancers, and buffers. The formulations are applied topically to the eye of a mammal suffering from glaucoma or ocular hypertension 1–4 times daily according to the routine discretion of a skilled clinician.

The estrogen metabolites can also be administered orally at concentrations from 10 milligram (mg)–1 gram (g)/kilogram (kg)/day body weight.

The preferred estrogen metabolites are 2-methoxyestradiol and 2-hydroxyestradiol.

The following examples illustrate various suitable formulations useful for lowering intraocular pressure.

EXAMPLE 1

| Component | wt. % |
| --- | --- |
| 2-Hydroxyestradiol | 1.00% |
| Mannitol | 2.40% |
| Sodium chloride | 0.40% |
| Carbopol 974P | 0.50% |
| Polysorbate 80 | 0.05% |
| Edetate disodium | 0.01% |
| Benzalkonium chloride | 0.01% + 5% XS |
| Sodium hydroxide | adjust pH to 7.2 |
| Purified water | qs to 100% |

This formulation is made according to methods known to those skilled in the art of ophthalmic pharmaceuticals formulation.

EXAMPLE 2

| Component | wt. % |
| --- | --- |
| 2-Methoxyestradiol | 1.0% |
| Tyloxapol | 0.01–0.05% |
| HPMC | 0.5% |
| Benzalkonium chloride | 0.01% |
| Sodium chloride | 0.8% |
| Edetate disodium | 0.01% |
| NaOH/HCl | q.s. pH 7.4 |
| Purified water | q.s. 100 mL |

The above formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1M NaOH/HCl. The solution is then sterilized by means of filtration.

2-Methoxyestradiol is sterilized by either dry heat or ethylene oxide. If ethylene oxide sterilization is selected, aeration for at least 72 hours at 50° C. is necessary. The sterilized steroid is weighed aseptically and placed into a pressurized ballmill container. The tyloxapol, in sterilized aqueous solution form, is then added to the ballmill container. Sterilized glass balls are then added to the container and the contents of the container are milled aseptically at 225 rpm for 16 hours, or until all particles are in the range of approximately 5 microns.

Under aseptic conditions, the micronized drug suspension formed by means of the preceding step is then poured into the HPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl.

EXAMPLE 3

FORMULATION FOR ORAL ADMINISTRATION

Tablet:

10–1000 mg of estrogen metabolite with inactive ingredients such as starch, lactose and magnesium stearate can be formulated according to procedures known to those skilled in the art of tablet formulation.

I claim:

1. A method for lowering and controlling intraocular pressure by administering a pharmaceutically effective amount of an estrogen metabolite.

2. The method of claim 1 wherein the estrogen metabolite has the formula:

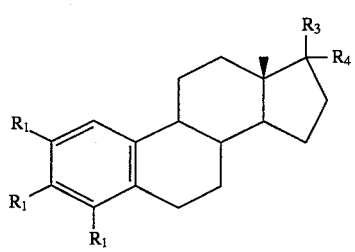

wherein:

$R_1$ is H, OH, $OR_2$, $R_2$;

$R_2$ is $C_1$–$C_6$ alkyl;

$R_3$ is OH, =O, $R_1$;

$R_4$ is $R_1$, C≡CH, C=$CH_2$; and pharmaceutically acceptable esters.

3. The method of claim 2 wherein the estrogen metabolite is selected from the group consisting of: 2-methoxyestradiol, 2-hydroxyestradiol, 4-methoxyestradiol, 2-methoxyestradiol 3-methyl ether, 2-hydroxyestrone, and 2-methoxyestrone.

4. The method of claim 1 wherein the estrogen metabolite is administered topically to the eye.

5. The method of claim 4 wherein the concentration of the estrogen metabolite is about 0.05–5 wt./vol. %.

6. The method of claim 1 wherein the estrogen metabolite is administered orally.

7. The method of claim 6 wherein the concentration of the estrogen metabolite is from about 10 mg-1g/kg body weight/day.

8. The method of claim 2 wherein the estrogen metabolite is administered topically to the eye.

9. The method of claim 2 wherein the concentration of the estrogen metabolite is about 0.05–5 wt./vol. %.

10. The method of claim 2 wherein the estrogen metabolite is administered orally.

11. The method of claim 2 wherein the concentration of the estrogen metabolite is from about 10 mg-1g/kg body weight/day.

* * * * *

UNITED STATES PATENT AND TRADEMARK OFFICE
CERTIFICATE OF CORRECTION

PATENT NO. : 5,521,168
DATED : May 28, 1996
INVENTOR(S) : Clark

It is certified that error appears in the above-identified patent and that said Letters Patent is hereby corrected as shown below:

Column 1, line 14, change "*Norethynodref*" to [*Norethynodrel*].

Column 1, line 23, change "anglogenesis" to [angiogenesis].

Column 1, lines 53 and 55, change "carbochol" to [carbachol].

Signed and Sealed this

Twenty-second Day of October, 1996

Attest:

BRUCE LEHMAN

Attesting Officer  Commissioner of Patents and Trademarks